United States Patent [19]

Tsugita et al.

[11] Patent Number: 4,983,304

[45] Date of Patent: Jan. 8, 1991

[54] MEMBRANE FOR SEPARATION OF WATER-ALCOHOL MIXED LIQUID AND PROCESS FOR PREPARATION THEREOF

[75] Inventors: Takashi Tsugita; Shinya Takeuchi, both of Marugame; Koichi Doi, Tokyo; Fumito Kishimoto, Tokuyama, all of Japan

[73] Assignees: Tokuyama Soda Kabushiki Kaisha, Yamaguchi; Katokichi Co., Ltd., Kagawa, both of Japan

[21] Appl. No.: 437,176

[22] Filed: Nov. 16, 1989

[30] Foreign Application Priority Data

Nov. 16, 1988 [JP] Japan ................................ 63-289195

[51] Int. Cl.$^5$ .............................................. B01D 71/08
[52] U.S. Cl. ................................ 210/640; 210/500.28
[58] Field of Search ................ 210/640, 500.28, 500.23

[56] References Cited

U.S. PATENT DOCUMENTS 4,808,313 2/1989 Michizuki et al. ............. 210/500.28

FOREIGN PATENT DOCUMENTS

| | | |
|---|---|---|
| 61-93802 | 5/1986 | Japan . |
| 62-4407 | 1/1987 | Japan . |
| 62-7403 | 1/1987 | Japan . |
| 63-39281 | 8/1988 | Japan . |

*Primary Examiner*—Frank Spear
*Attorney, Agent, or Firm*—Sherman and Shalloway

[57] ABSTRACT

Disclosed is a membrane for the separation of a water-alcohol mixed liquid by the pervaporation method, which is composed of a chitosan having a molecular weight of 80,000 to 150,000 and a deacetylation degree adjusted to 80 to 95%. This separating membrane has an excellent selective permeability to water in the separation of a water-alcohol mixed liquid, and the mechanical strength of this separating membrane is very high. This separating membrane can be prepared by a process comprising dissolving a chitosan having a molecular weight of 80,000 to 150,000 and a deacetylation degree adjusted to 80 to 95% in an acidic aqueous solution to form a dope having a chitosan concentration of 9 to 12% by weight, shaping the dope into a membrane and immersing the membrane in an alkaline solution.

13 Claims, No Drawings

MEMBRANE FOR SEPARATION OF WATER-ALCOHOL MIXED LIQUID AND PROCESS FOR PREPARATION THEREOF

BACKGROUND OF THE INVENTION (1) Field of the Invention

The present invention relates to a membrane for the separation of a water-alcohol mixed liquid and a process for the preparation thereof. More particularly, the present invention relates to a membrane suitable for separating a water-alcohol mixed liquid by the pervaporation method and a process for the preparation of this separating membrane.

(2) Description of the Related Art

Distillation has been mainly utilized for the separation of a water-alcohol mixed liquid, but this distillation process is defective in that the energy cost is large and since a water-alcohol mixed liquid often has an azeotropic composition, the separation is insufficient.

Accordingly, various separating methods using a membrane have attracted attention, and various membranes for use in separating water-alcohol mixed liquids by the pervaporation method (a liquid mixture is supplied into the primary side, the pressure in the secondary side separated from the primary side through a separating membrane is reduced, and a certain component in the liquid mixture is selectively diffused into the secondary side and recovered in the form of a vapor in the secondary side) have been reported. For example, the specification of U.S. Pat. No. 2,953,502 discloses the separation of an azeotropic liquid mixture of water and ethyl alcohol or the like by using a cellulose acetate membrane or the like as the separating membrane, J. Polym. Sci., Symposium No. 41, pages 145–153 (1973) discloses the separation of a water-methanol mixed liquid by using a separating membrane of cellophane, and J. Applied Polym. Sci., vol. 26, pages 3223–3243 (1981) discloses the separation of a water-methanol mixed liquid by using a separating membrane of grafted polyvinyl alcohol. However, the separation of water-alcohol mixed liquids by the prevaporation method using these separating membranes is defective in that the ratio of separation by one permeation of the water-alcohol mixed liquid through the separating membrane, that is, the separation coefficient, is small and the quantity of permeation through the separating membrane is small, and therefore, the separation performances are insufficient.

As the means for solving these problems of the conventional separating membranes to be used in the pervaporation method, a separating membrane composed of chitosan, which is a natural cationic polymer, has recently been proposed. For example, Japanese Patent Application Laid-Open Specification No. 56-190706 (Japanese Patent Publication No. 63-39281) discloses a process in which a liquid mixture of water and ethanol or the like is separated by the pervaporation method using a chitosan type membrane, Japanese Patent Application Laid-Open Specification No. 62-4407 discloses a separating membrane for the pervaporation, which is composed of a polymer obtained by polymerizing a vinyl monomer to a chitosan compound, and Japanese Patent Application Laid-Open Specification No. 63-7403 discloses a separating membrane for the pervaporation which is composed of a chitosan salt or chitosan derivative salt. Separating membranes composed of chitosan compounds exert considerable separation performances in the separation of water-alcohol mixed liquids by the pervaporation, but no satisfactory results can be obtained on an industrial scale and especially, it is desired that the separation coefficient will be further improved. The separation coefficient ($\alpha$) referred to herein is represented by the following equation.

$$\alpha_B{}^A = \frac{(W_A/W_B) \text{ in permeated liquid}}{(W_A/W_B) \text{ in supplied liquid}}$$

As is apparent from the above equation, the separation coefficient is the ratio of the weight ratio ($W_A/W_B$) between the components A and B in the permeated liquid after the permeation to the weight ratio ($W_A/W_B$) in the supplied liquid before the permeation. When water is regarded as the base (component A), if $\alpha$ is larger than 1, water is selectively permeated, and the larger is the value $\alpha$, the higher is the selective permeability.

SUMMARY OF THE INVENTION

It is a primary object of the present invention to provide a separating membrane composed of chitosan for the separation of a water-alcohol mixed liquid by the pervaporation method, which is especially excellent in the selective water permeability (the improved water separation coefficient).

Another object of the present invention is to provide a process for the preparation of a separating membrane composed of chitosan for the separation of a water-alcohol mixed liquid by the pervaporation method, which is especially excellent in the selective water permeability (the improved water separation coefficient).

Still another object of the present invention is to provide a process in which a water-alcohol mixed liquid can be effectively separated by the pervaporation method.

A further object of the present invention is to provide a process which exhibits such a separation performance that when a water-ethanol mixed liquid having an ethanol concentration of at least 80% by weight is separated by the pervaporation, the ethanol concentration can be reduced below 0.002% by weight in the permeated liquid, or the separation coefficient is at least 100,000, and a separating membrane for use in carrying out this process.

In accordance with one fundamental aspect of the present invention, there is provided a membrane for the separation of a water-alcohol mixed liquid by the pervaporation method, which is composed of a chitosan having a molecular weight of 80,000 to 150,000 and a deacetylation degree adjusted to 80 to 95%.

In accordance with another aspect of the present invention, there is provided a process for the preparation of a separating membrane as set forth above, which comprises dissolving a chitosan having a molecular weight of 80,000 to 150,000 and a deacetylation degree adjusted to 80 to 95% in an acidic aqueous solution to form a dope having a chitosan concentration of 9 to 12% by weight, shaping the dope into a membrane and immersing the membrane in an alkaline solution.

Other objects, features and advantages will become apparent from the following detailed description.

DETAILED DESCRIPTION OF THE INVENTION

Chitin is a linear polysaccharide constituting the pellicle (shell) which is a supporting tissue of a crustacean such as a crab, a prawn or shrimp, or a fungus, and it is conjectured that about one hundred billion tons of chitin is biologically produced on the earth in a year, and chitin is an organic resource present in a largest quantity in a substantially non-utilized state. Chitosan is prepared by deacetylating chitin and is a cationic polymer soluble in a dilute acid, while chitin is hardly soluble in a solvent. In the industry, chitosan is not substantially utilized except that chitosan is marketed as a flocculating agent, and effective utilization of chitosan has been investigated in various fields.

In general, the organic solvent resistance of chitosan is much higher than those of synthetic polymers, and chitosan is excellent in the utilizability for an organic liquid-separating membrane. Moreover, since chitosan contains reactive amino and hydroxyl groups in the molecule, introduction of a variety of functional groups or crosslinking can be easily accomplished, and it is expected that the separation capacity or membrane strength will be improved.

As pointed out herein before, a trial has been made to use chitosan as a material of a membrane for separating a water-alcohol mixed liquid. According to this trial, a membrane is prepared by the dry process comprising casting a dilute acid solution of chitosan, drying the cast solution to form a membrane and neutralizing the formed membrane in an alkaline coagulating solution. However, according to this dry process, a chitosan membrane having a high separating capacity to a water-alcohol mixed liquid in the pervaporation method cannot be obtained, and from the industrial viewpoint, this drying process is defective in that mass production is impossible and the cost increases. Separately, a wet process has been tried comprising casting a dilute acid solution of chitosan and immersing the cast solution in a coagulating solution to form a membrane. However, if the molecular weight of chitosan is too high, the viscosity of the solution is too high and only a dope having a low concentration can be obtained, and the obtained membrane becomes porous. In case of chitosan having a low molecular weight, formation of a membrane according to the wet process is difficult, and even if a membrane can be formed, the mechanical strength of the membrane is extremely low. When chitosan having a deacetylation degree of almost 100% is used, a high separating capacity cannot be obtained and shrinkage is caused at the drying step, and the membrane-forming property of this chitosan is insufficient.

We made research with a view to solving the foregoing problems, and as the result, it was found that if a shell of prawn or shrimp is used as a preferable starting material, a chitosan having a molecular weight of 80,000 to 150,000 and a deacetylation degree adjusted to 80 to 95% is prepared from this starting material, a dope of this chitosan having a concentration of 9 to 12% by weight is formed into a membrane by the wet process and a water-alcohol mixed liquid is separated by the obtained membrane by the pervaporation method, an especially high separation coefficient is attained and a selective water permeability of almost 100% can be obtained at an ethanol concentration higher than 50% by weight. We have now completed the present invention based on this finding.

Namely, in the present invention, it is indispensable that a chitosan having a molecular weight of 80,000 to 150,000 and a deacetylation degree adjusted to 80 to 95% should be used and in the preparation of a membrane, a dope of this chitosan having a concentration of 9 to 12% by weight should be formed and used. If any one of these conditions is not satisfied, an intended membrane having a high separation coefficient and a high mechanical strength cannot be obtained. For example, if a chitosan having a molecular weight lower than 80,000 is used, pinholes are formed in the obtained membrane, and the mechanical strength and the separation coefficient are reduced. If a chitosan having a molecular weight higher than 150,000 is used, as pointed out hereinbefore, the viscosity of the chitosan solution is high and only a dope having a low concentration is obtainable, and therefore, formation of a membrane by the wet process becomes difficult and a membrane having a high separating capacity cannot be obtained. Furthermore, if a chitosan having a molecular weight of 80,000 to 150,000 but a deacetylation degree lower than 80% is used, since the amount of the amino group in the chitosan is small, the separation coefficient of the obtained membrane is insufficient, and the permeation quantity of the liquid is small. If a chitosan having a molecular weight of 80,000 to 150,000 but a deacetylation degree higher than 95% is used, since the amount of the amino group in the chitosan is too large, the mechanical strength of the obtained membrane is insufficient and the separation coefficient is low. Furthermore, even in the case where a chitosan having a molecular weight of 80,000 to 150,000 and a deacetylation degree of 80 to 95% is used, if the concentration of the chitosan in the dope is lower than 8% by weight, a membrane having a high separating capacity cannot be obtained by the wet process, and if the concentration of the chitosan is higher than 12% by weight, the viscosity of the chitosan solution increases and hence, formation of a membrane by the wet process is difficult.

According to the present invention, since a dope having a high chitosan concentration is used, a membrane can be formed by the wet process comprising casting the dope and immersing the cast dope in a coagulating solution, and not only a flat membrane but also a hollow tube or fiber membrane of chitosan, formation of which is difficult according to the conventional technique, can be formed according to the present invention.

The process for the preparation of the separating membrane of the present invention will now be described in detail.

The process for obtaining a chitosan having a molecular weight of 80,000 to 150,000 and a deacetylation degree of 80 to 95%, which is used in the present invention, is not particularly critical. However, there can be adopted, for example, a process in which chitin obtained by removing calcium salts, proteins and the like from a crab shell or a shell of prawn or shrimp is treated with an acid or the like so that when the chitin is converted to chitosan, the molecular weight is 80,000 to 150,000, and the treated chitin is treated with a concentrated alkali to form a chitosan having a deacetylation degree of 80 to 95%. The adjustment of the molecular weight of chitosan is accomplished by the hydrolysis at the acid or alkali treatment. The molecular weight referred to herein is one determined from the value of the peak top of a GPC chromatogram obtained under the following conditions by using pullulan as the reference substance:

Column: TSK 66000GWXL+GMPWXL
eluent phase: 0.2M acetic acid buffer having a pH value of 4.0 (containing 0.3% of triethanol amine and 0.1M sodium chloride)
Flow rate: 0.5 ml/min
Temperature: 40° C.
Detector: refractometer The deacetylation degree is determined by using a 0.5% solution of chitosan in 0.2M acetic acid buffer having a pH value of 4.0 as a sample and carrying out colloid titration with 1/400N PVSK (potassium polyvinyl sulfate) by using Toluidine Blue as an indicator.

According to the process for the preparation of the separating membrane of the present invention, a chitosan having a molecular weight of 80,000 to 150,000 and a deacetylation degree adjusted to 80 to 95%, which is prepared in the above-mentioned manner, is dissolved in a solvent such as an acidic aqueous solution to obtain a dope having a chitosan concentration of 9 to 12% by weight, and after or simultaneously with shaping of the dope into a desired membrane form, the dope is immersed into a coagulating bath composed of an alkaline solution without drying according to the known wet process. An organic acid such as formic acid or acetic acid is preferably used for the acidic aqueous solution as the solvent. As the alkaline solution as the coagulating solution, there can be used, for example, a solution formed by dissolving an alkaline substance such as sodium hydroxide, potassium hydroxide, sodium carbonate, potassium carbonate or ammonia in water, an alcohol such as methanol or ethanol or a water-alcohol mixture. The thickness of the membrane depends on the intended durability and permeation liquid quantity. In the case of sheet membrane, the thickness of the membrane is generally adjusted to 1 to 100 $\mu$m and preferably to 3 to 50 $\mu$m, and in the case of the hollow tube of fiber, the outer diameter is 50 $\mu$m to 5 mm and the thickness is 10 to 500 $\mu$m.

More specifically, when a sheet (flat) membrane is prepared, the starting chitosan is dissolved in a 0.6N to 1N aqueous solution of acetic acid at a concentration of 9 to 12% by weight to form a dope, and the dope is filtered, deaerated and cast on a glass sheet by using an applicator. Then, the glass sheet having the dope cast thereon is immersed in a coagulating bath comprising ethanol, water and sodium hydroxide at a weight ratio of 6/3/1 to form a membrane by the wet process. Then, the formed membrane is washed with water sufficiently repeatedly and dried at room temperature to obtain a chitosan membrane.

When a hollow tube of fiber membrane is prepared, the same dope as mentioned above with respect to the preparation of a flat membrane is charged in a spinning tank and pressurized, and the pressurized dope is extruded into the coagulating bath through a hollow tube of fiber forming nozzle and simultaneously, a gas such as nitrogen is caused to flow in the inner side of the membrane. Then, the extrudate is continuously passed through the water-washing and drying steps to obtain a membrane by the wet process. It is preferred that at the drying step, the membrane is dried at room temperature while applying a certain tension to the membrane. This tension is within the range of 15 to 1500 g/mm$^2$, preferably 30 to 200 g/mm$^2$. A sheet (flat) membrane can be continuously prepared by the wet process by using a slit instead of the above-mentioned nozzle.

In the above-mentioned wet process for the preparation of the separating membrane according to the present invention, by increasing the chitosan concentration in the dope to 9 to 12% by weight by adjusting the molecular weight of the starting chitosan, formation of a porous membrane can be prevented, and it is considered that by adjusting the deacetylation degree of the starting chitosan to 80 to 95% by weight, the microstructure is changed and a high separating capacity can be obtained.

The chitosan membrane of the present invention can be chemically modified by ionization, crosslinking or the like. For example, the chemical resistance and heat resistance can be improved by imparting an ion-crosslinked structure or covalent crosslinked structure to the membrane by ionization using an anion such as a sulfuric acid group or a phosphoric acid group, or crosslinking using a diepoxy compound, a dialdehyde compound such as glutaraldehyde, or an isocyanate compound.

When the membrane of the present invention is used for the separation of a water-alcohol mixed liquid, water is selectively permeated, and the water separation coefficient is much improved over the water separation coefficient attainable by the conventional technique. Especially, if the ethanol concentration in the supplied liquid is higher than 80% by weight, the separation coefficient is substantially infinitely large in a broad temperature range of 25° to 70° C. Furthermore, the permeation flux is relatively high in a broad temperature range including room temperature. The reason is considered to be that by specifically adjusting the molecular weight and deacetylation degree of the chitosan in the above-mentioned manner, the chitosan molecule is placed in the state suitable for selective permeation of water.

When the separating membrane of the present invention is used, it is expected that a water-alcohol mixed liquid will be separated with an energy corresponding to $\frac{1}{4}$ to $\frac{1}{3}$ of the energy required in the conventional distillation method. Namely, the separating membrane of the present invention is effectively used for concentration of ethanol and dehydration/purification of mixed organic solvents in the industry of the production of alcohols and in the brewing and fermentation industry and for regeneration of alcohols in the organic synthesis chemical industry. Especially, since a high separating capacity and a high permeation speed can be obtained in a broad temperature range including room temperature, the separating membrane of the present invention is effectively used for removal of water from a bioreactor utilizing an enzyme reaction. Accordingly, the utilization range can be greatly expanded.

Still further, since a hollow tube (fiber) type membrane module is advantageous over a sheet (flat) membrane module in that a compact apparatus can be designed with the same effective membrane area, the membrane can be utilized in a narrow space in a room where a large apparatus cannot be set.

The present invention will now be described in detail with reference to the following examples that by no means limit the scope of the invention.

EXAMPLE 1

To 450 g of a 1N aqueous solution of acetic acid was added 50 g of chitosan powder obtained from a prawn shell, which had a molecular weight of 145,000 and a deacetylation degree of 89.4%, and the liquid was stirred at a chitosan concentration of 10% by weight overnight at 25° C. to form a solution. The solution was filtered through a glass filter G2 and deaerated under reduced pressure by an aspirator. The obtained chitosan dope was cast on a glass sheet having a size of 200 mm×200 mm by using an applicator and immersed in a coagulating bath (comprising ethanol, water and sodium hydroxide at a weight ratio of 6/3/1) for 1.5 hours. The formed flat membrane was sufficiently washed with water and dried at room temperature to obtain a membrane composed of chitosan, which had a thickness of 18 μm.

An aqueous solution containing 92% by weight of ethanol and an aqueous solution containing 85% by weight of isopropanol were separated by using the obtained chitosan membrane as the separating membrane according to the pervaporation method. The separation was conducted under conditions of a temperature of 25° C., a supplied liquid quantity of 150 ml, a reduced pressure of 2 to 3 mm Hg and an effective membrane area of 28 cm$^2$. The permeation flux Q was determined by the weight method. The composition of the permeated liquid was determined by the quantitative analysis using a gas chromatograph. The alcohol detection limit of the gas chromatograph was 0.002%. The separation coefficient was expressed based on water. The obtained results are shown in Table 1.

TABLE 1

| Alcohol Concentration (%) in Supplied Liquid | Permeated Alcohol Concentration (%) | Separation Coefficient (α) | Permeation Flux (g/m$^2$ · hr) |
|---|---|---|---|
| 92% ethanol | <0.002 | >570000 | 6.2 |
| 85% isopropanol | <0.002 | >280000 | 14.2 |

EXAMPLE 2

In the same manner as described in Example 1, chitosan powder having a molecular weight of 120,000 and a deacetylation degree of 95%, which was obtained from a prawn shell, was dissolved in a 1N aqueous solution of acetic acid to obtain a chitosan dope having a concentration of 10% by weight. In the same manner as described in Example 1, a sheet (flat) membrane composed of chitosan, which had a thickness of 18 μm, was prepared from this dope.

An aqueous solution containing 92% by weight of ethanol and an aqueous solution containing 85% by weight of isopropanol were separated by using the obtained chitosan membrane as the separating membrane under the same conditions as described in Example 1 according to the pervaporation method. The obtained results are shown in Table 2.

TABLE 2

| Alcohol Concentration (%) in Supplied Liquid | Permeated Alcohol Concentration (%) | Separation Coefficient (α) | Permeation Flux (g/m$^2$ · hr) |
|---|---|---|---|
| 92% ethanol | <0.002 | >570000 | 5.8 |
| 85% isopropanol | <0.002 | >280000 | 13.3 |

EXAMPLE 3

In the same manner as described in Example 1, chitosan powder having a molecular weight of 90,000 and a deacetylation degree of 95%, which was obtained from a prawn shell, was dissolved in a 1N aqueous solution of acetic acid to obtain a chitosan dope having a concentration of 10% by weight. In the same manner as described in Example 1, a sheet (flat) membrane composed of chitosan, which had a thickness of 18 μm, was prepared from this dope.

An aqueous solution containing 92% by weight of ethanol and an aqueous solution containing 85% by weight of isopropanol were separated by using the obtained chitosan membrane as the separating membrane under the same conditions as described in Example 1 according to the pervaporation method. The obtained results are shown in Table 3.

TABLE 3

| Alcohol Concentration (%) in Supplied Liquid | Permeated Alcohol Concentration (%) | Separation Coefficient (α) | Permeation Flux (g/m$^2$ · hr) |
|---|---|---|---|
| 92% ethanol | <0.002 | >570000 | 7.5 |
| 85% isopropanol | <0.002 | >280000 | 18.2 |

COMPARATIVE EXAMPLE 1

To 462.5 g of a 1N aqueous solution of acetic acid was added 37.5 g of chitosan powder having a molecular weight of 400,000 and a deacetylation degree of 100%, which was obtained from a prawn shell, and the liquid was stirred at a chitosan concentration of 7.5% by weight overnight at 25° C. to obtain a solution. The subsequent operations were carried out in the same manner as described in Example 1 to obtain a plain membrane composed of chitosan, which had a thickness of 18 μm.

By using this chitosan membrane as the separating membrane, an aqueous solution containing 92% by weight of ethanol and an aqueous solution containing 85% by weight of isopropanol were separated according to the pervaporation method under the same conditions as described in Example 1 except that the temperature was changed to 50° C. the obtained results are shown in Table 4.

TABLE 4

| Alcohol Concentration (%) in Supplied Liquid | Permeated Alcohol Concentration (%) | Separation Coefficient (α) | Permeation Flux (g/m$^2$ · hr) |
|---|---|---|---|
| 92% ethanol | 55 | 9.4 | 600 |
| 85% isopropanol | 8.4 | 62 | 688 |

COMPARATIVE EXAMPLE 2

Chitosan powder having the same manner molecular weight and deacetylation degree as described in Comparative Example 1 was dissolved in a 1N aqueous of acetic acid so that the chitosan concentration was 2% by weight. The solution was cast on a glass sheet and dried at 60° C. to obtain a membrane composed of chitosan acetate. The membrane was immersed in a 1N aqueous solution of sodium hydroxide to make neutralization, and was then washed with water and dried to obtain a chitosan membrane.

By using the obtained chitosan membrane as the separating membrane, an aqueous solution containing 90% by weight of ethanol was separated by the pervaporation method under conditions of a temperature of 40° C., a supplied liquid feed quantity of 20 ml and a reduced pressure of 10$^{-2}$ Torr. The other conditions were the same as those adopted in Example 1. As the result, it was found that the separation coefficient was 31 and the permeation flux was 120 g/m$^2$. hr.

COMPARATIVE EXAMPLE 3

In the same manner as described in Example 1, chitosan powder having a molecular weight of 50,000 and a deacetylation degree of 100%, which was obtained from a prawn shell, was dissolved in a 1N aqueous solution of acetic acid to obtain a chitosan dope having a concentration of 12% by weight. In the same manner as described in Example 1, a sheet (flat) membrane composed of chitosan, which had a thickness of 18 μm, was prepared from this dope.

An aqueous solution containing 92% by weight of ethanol and an aqueous solution containing 85% by weight of isopropanol were separated by using the obtained chitosan membrane as the separating membrane under the same conditions as described in Example 1 according to the pervaporation method. The obtained results are shown in Table 5.

TABLE 5

| Alcohol Concentration (%) in Supplied Liquid | Permeated Alcohol Concentration (%) | Separation Coefficient ($\alpha$) | Permeation Flux (g/m$^2$ · hr) |
| --- | --- | --- | --- |
| 92% ethanol | 29.4 | 28 | 210 |
| 85% isopropanol | 3.0 | 183 | 230 |

EXAMPLE 4

The chitosan membrane obtained in Example 1 was immersed in an aqueous solution containing 1% by weight of glutaraldehyde at room temperature for 1 hour to form a crosslinkage.

An aqueous solution containing 92% by weight of ethanol and an aqueous solution containing 85% by weight of isopropanol were separated by using the obtained crosslinked chitosan membrane as the separating membrane under the same conditions as described in Example 1 according to the pervaporation method. The obtained results are shown in Table 6.

TABLE 6

| Alcohol Concentration (%) in Supplied Liquid | Permeated Alcohol Concentration (%) | Separation Coefficient ($\alpha$) | Permeation Flux (g/m$^2$ · hr) |
| --- | --- | --- | --- |
| 92% ethanol | <0.002 | >570000 | 33.4 |
| 85% isopropanol | <0.002 | >280000 | 135.5 |

EXAMPLE 5

The chitosan membrane obtained in Example 2 was crosslinked in the same manner as described in Example 4. By using the obtained crosslinked chitosan membrane, the separation test was carried out in the same manner under the same conditions as described in Example 2. The obtained results are shown in Table 7.

TABLE 7

| Alcohol Concentration (%) in Supplied Liquid | Permeated Alcohol Concentration (%) | Separation Coefficient ($\alpha$) | Permeation Flux (g/m$^2$ · hr) |
| --- | --- | --- | --- |
| 92% ethanol | <0.002 | >570000 | 31.3 |
| 85% isopropanol | <0.002 | >280000 | 127 |

EXAMPLE 6

The chitosan membrane obtained in Example 3 was crosslinked in the same manner as described in Example 4. By using the obtained crosslinked chitosan membrane, the separation test was carried out in the same manner under the same conditions as described in Example 3. The obtained results are shown in Table 8.

TABLE 8

| Alcohol Concentration (%) in Supplied Liquid | Permeated Alcohol Concentration (%) | Separation Coefficient ($\alpha$) | Permeation Flux (g/m$^2$ · hr) |
| --- | --- | --- | --- |
| 92% ethanol | <0.002 | >570000 | 40.2 |
| 85% isopropanol | <0.002 | >280000 | 162 |

COMPARATIVE EXAMPLE 4

The chitosan membrane obtained in Comparative Example 2 was crosslinked with glutaraldehyde in the same manner as described in Example 2.

An aqueous solution containing 90% by weight of ethanol was separated by using the obtained crosslinked chitosan membrane by the pervaporation method under the same conditions as described in Comparative Example 2. As the result, it was found that the separation coefficient was 505 and the permeation flux was 60 g/m$^2$. hr.

EXAMPLE 7

By using the crosslinked chitosan membrane obtained in Example 4, aqueous solutions of ethanol having concentrations shown in Table 9 were separated by the pervaporation method in the same manner under the same conditions as described in Example 4. The obtained results are shown in Table 9.

TABLE 9

| Alcohol Concentration (%) in Supplied Liquid | Permeated Alcohol Concentration (%) | Separation Coefficient ($\alpha$) | Permeation Flux (g/m$^2$ · hr) |
| --- | --- | --- | --- |
| 10% ethanol | 0.70 | 16 | 1899 |
| 30% ethanol | 0.56 | 76 | 895 |
| 50% ethanol | 0.034 | 2940 | 488 |
| 70% ethanol | <0.002 | >110000 | 249 |
| 90% ethanol | <0.002 | >440000 | 83 |
| 96% ethanol | <0.002 | >1190000 | 16 |

EXAMPLE 8

By using the crosslinked chitosan membrane obtained in Example 4 as the separating membrane, aqueous solutions of ethanol having concentrations shown in Table 10 were separated by the pervaporation method in the same manner under the same conditions as described in Example 4 except that the temperature was changed to 55° C. The obtained results are shown in Table 10.

TABLE 10

| Alcohol Concentration (%) in Supplied Liquid | Permeated Alcohol Concentration (%) | Separation Coefficient ($\alpha$) | Permeation Flux (g/m$^2$ · hr) |
| --- | --- | --- | --- |
| 70% ethanol | 0.024 | 9700 | 733 |
| 80% ethanol | <0.002 | >190000 | 359 |
| 85% ethanol | <0.002 | >280000 | 231 |
| 90% ethanol | <0.002 | >440000 | 146 |
| 95% ethanol | <0.002 | >940000 | 29.9 |
| 97% ethanol | <0.002 | >1610000 | 11.4 |
| 99% ethanol | <0.002 | >4940000 | 4.9 |

EXAMPLE 9

By using the crosslinked chitosan membrane obtained in Example 4 as the separating membrane, aqueous solutions of ethanol having concentrations shown in Table 11 were separated by the pervaporation method in the same manner under the same conditions as described in Example 4 except that the temperature was changed to 70° C. The obtained results are shown in Table 11.

TABLE 11

| Alcohol Concentration (%) in Supplied Liquid | Permeated Alcohol Concentration (%) | Separation Coefficient ($\alpha$) | Permeation Flux ($g/m^2 \cdot hr$) |
| --- | --- | --- | --- |
| 70% ethanol | 0.245 | 950 | 1170 |
| 80% ethanol | 0.007 | 59000 | 573 |
| 85% ethanol | <0.002 | >280000 | 345 |
| 90% ethanol | <0.002 | >440000 | 150 |
| 95% ethanol | <0.002 | >940000 | 37.2 |
| 97% ethanol | <0.002 | >1610000 | 21.1 |
| 99% ethanol | <0.002 | >4940000 | 9.8 |

EXAMPLE 10

Chitosan powder having a molecular weight of 145,000 and a deacetylation degree of 89.5%, which was used in Example 1, was dissolved in an aqueous solution of acetic acid to obtain a chitosan solution (dope) having a concentration of 10% by weight. The dope was supplied to a spinning nozzle for forming a hollow tube, which consisted of an outer tube having an inner diameter of 1 mm and an inner tube having an outer diameter of 0.8 mm and an inner diameter of 0.4 mm, and, was extruded at a spinning speed of 20 m/min into a coagulating bath having the same composition as described in Example 1. Incidentally, nitrogen gas was supplied into the inner side of the membrane. The obtained membrane was sufficiently washed with water and dried at room temperature under a tension of 15 g/min$^2$ to obtain a hollow tube membrane composed of chitosan, which had a hollow tube inner diameter of 0.8 mm. The chitosan hollow tube membrane was crosslinked with glutaraldehyde and then assembled into a membrane module (A type). Separately, the chitosan hollow yarn membrane was first assembled into a membrane module and then crosslinked with glutaraldehyde (B type).

By using each of the so-obtained membrane modules having an effective membrane area of 440 cm$^2$, an aqueous solution containing 90% by weight of ethanol was separated under the same conditions as described in Example 1. The obtained results are shown in Table 12.

TABLE 12

| Type of Membrane | Permeated Alcohol Concentration (%) | Separation Coefficient ($\alpha$) | Permeation Flux ($g/m^2 \cdot hr$) |
| --- | --- | --- | --- |
| A | <0.002 | >440000 | 63.7 |
| B | <0.002 | >440000 | 86.4 |

EXAMPLE 11

By using the crosslinked chitosan hollow tube membrane (having an effective membrane length of 10 cm and an effective membrane area of 440 cm$^2$) obtained in Example 10, an aqueous solution of ethanol having a concentration of 80, 90 or 97% by weight was separated at a temperature of 25°, 55° or 70° C. by the pervaporation method. Other conditions were the same as adopted in Example 1. The obtained results are shown in Table 13.

TABLE 13

| Supplied Ethanol Concentration (% by weight) | 25° C. | | 55° C. | | 70° C. | |
| --- | --- | --- | --- | --- | --- | --- |
| | Separation Coefficient ($\alpha$) | Permeation Flux ($g/m^2 \cdot hr$) | Separation Coefficient ($\alpha$) | Permeation Flux ($g/m^2 \cdot hr$) | Separation Coefficient ($\alpha$) | Permeation Flux ($g/m^2 \cdot hr$) |
| 80 | >190000 | 220 | >190000 | 428 | >190000 | 677 |
| 90 | >440000 | 84.9 | >440000 | 153 | >440000 | 170 |
| 97 | >1610000 | 8.5 | >1610000 | 12.7 | >1610000 | 12.7 |

EXAMPLE 12

The procedures of Example 11 were repeated in the same manner except that aqueous solutions of methanol shown in Table 14 were separated instead of the aqueous solutions of ethanol. The obtained results are shown in Table 14.

TABLE 14

| Supplied Methanol Concentration (% by weight) | 25° C. | | 55° C. | |
| --- | --- | --- | --- | --- |
| | Separation Coefficient ($\alpha$) | Permeation Flux ($g/m^2 \cdot hr$) | Separation Coefficient ($\alpha$) | Permeation Flux ($g/m^2 \cdot hr$) |
| 80 | 270 | 35.4 | 48 | 185.8 |
| 90 | 60000 | 9.2 | 99 | 55.6 |
| 97 | >1610000 | 3.5 | >1610000 | 7.4 |

EXAMPLE 13

A membrane module (A type) having an effective membrane length of 30 cm and an effective membrane area of 1320 cm$^2$ was assembled by using the same crosslinked chitosan hollow tube membrane as obtained in Example 10.

By using the obtained hollow tube membrane module, aqueous solutions of ethanol were separated by the pervaporation method in the same manner as described in Example 10. The obtained results are shown in Table 15.

TABLE 15

| Supplied Ethanol Concentration (% by weight) | 25° C. | | 55° C. | | 70° C. | |
|---|---|---|---|---|---|---|
| | Separation Coefficient ($\alpha$) | Permeation Flux (g/m² · hr) | Separation Coefficient ($\alpha$) | Permeation Flux (g/m² · hr) | Separation Coefficient ($\alpha$) | Permeation Flux (g/m² · hr) |
| 80 | >190000 | 139 | >190000 | 413 | >190000 | 620 |
| 90 | >440000 | 84.9 | >440000 | 129 | >440000 | 147 |
| 97 | >1610000 | 5.0 | >1610000 | 5.7 | >1610000 | 7.1 |

COMPARATIVE EXAMPLE 5

To 450 g of a 1N aqueous solution of acetic acid was added 50 g of chitosan powder having a molecular weight of 105,000 and a deacetylation degree of 100%, which was obtained from a prawn shell, and the liquid was stirred at a chitosan concentration of 10% by weight overnight at 25° C. to form a chitosan solution. By using the obtained chitosan solution, a hollow tube membrane was formed in the same manner as described in Example 10 and a membrane module was assembled. The membrane module was crosslinked with glutaraldehyde.

An aqueous solution containing ethanol at a concentration of 90% by weight was separated at a temperature of 25° or 50° C. by using the crosslinked membrane module according to the pervaporation method under the same conditions as described in Example 1. The obtained results are shown in Table 16.

TABLE 16

| Supplied Ethanol Concentration (% by weight) | 25° C. | | 55° C. | |
|---|---|---|---|---|
| | Separation Coefficient ($\alpha$) | Permeation Flux (g/m² · hr) | Separation Coefficient ($\alpha$) | Permeation Flux (g/m² · hr) |
| 90 | 106 | 78 | 114 | 73 |

COMPARATIVE EXAMPLE 6

In the same manner as described in Example 1, 30 g of chitosan powder having a molecular weight of 45,000 and a deacetyation degree of 89.4%, which was obtained from a prawn shell, was dissolved in 470 g of a 1N aqueous solution of acetic acid to obtain a chitosan dope having a concentration of 6% by weight. In the same manner as described in Example 1, a membrane composed of chitosan was prepared from this dope.

By using the obtained chitosan membrane as the separating membrane, aqueous solutions of alcohols were separated by the pervaporation method under the same conditions as described in Example 1. The obtained results are shown in Table 17.

TABLE 17

| Alcohol Concentration (%) in Supplied Liquid | Permeated Alcohol Concentration (%) | Separation Coefficient ($\alpha$) | Permeation Flux (g/m² · hr) |
|---|---|---|---|
| 92% ethanol | 58.1 | 8.3 | 635 |
| 85% isopropanol | 9.4 | 54.6 | 720 |

EXAMPLE 14

To 450 g of a 1N aqueous solution of acetic acid was added 50 g of chitosan powder having a molecular weight of 105,000 and a deacetylation degree of about 90%, which was obtained from a prawn shell, and the liquid was stirred at a chitosan concentration of 10% by weight overnight at 25° C. to form a chitosan solution. By using the obtained chitosan solution, a hollow tube membrane was formed in the same manner as described in Example 10 and a membrane module was assembled. The membrane module was crosslinked with glutaraldehyde.

An aqueous solution containing ethanol at a concentration of 90% by weight was separated at a temperature of 25° or 50° C. by using the crosslinked membrane module according to the pervaporation method under the same conditions as described in Example 1. The obtained results are shown in Table 18.

TABLE 18

| Supplied Ethanol Concentration (% by weight) | 25° C. | | 55° C. | |
|---|---|---|---|---|
| | Separation Coefficient ($\alpha$) | Permeation Flux (g/m² · hr) | Separation Coefficient ($\alpha$) | Permeation Flux (g/m² · hr) |
| 90 | >440000 | 89.5 | >440000 | 204.8 |

COMPARATIVE EXAMPLE 7

A chitosan membrane was prepared in the same manner as described in Example 1 except that chitosan powder having a molecular weight of 145,000 and a deacetylation degree of 100%, which was obtained from a prawn shell, was used.

By using the obtained chitosan membrane as the separating membrane, aqueous solutions of alcohol were separated by the pervaporation method under the same conditions as described in Example 1. The obtained results are shown in Table 19.

TABLE 19

| Alcohol Concentration (%) in Supplied Liquid | Permeated Alcohol Concentration (%) | Separation Coefficient (α) | Permeation Flux (g/m²·hr) |
| --- | --- | --- | --- |
| 92% ethanol | 8.4 | 125 | 6.5 |
| 85% isopropanol | 0.7 | 804 | 15.3 |

COMPARATIVE EXAMPLE 8

A chitosan membrane was prepared in the same manner as described in Example 1 except that chitosan powder having a molecular weight of 145,000 and a deacetylation degree of 60%, which was obtained from a prawn shell, was used.

By using the obtained chitosan membrane as the separating membrane, aqueous solutions of alcohols were separated by the pervaporation method under the same conditions as described in Example 1. The obtained results are shown in Table 20.

TABLE 20

| Alcohol Concentration (%) in Supplied Liquid | Permeated Alcohol Concentration (%) | Separation Coefficient (α) | Permeation Flux (g/m²·hr) |
| --- | --- | --- | --- |
| 92% ethanol | 12.3 | 82 | 5.7 |
| 85% isopropanol | 1.0 | 561 | 13.1 |

COMPARATIVE EXAMPLE 9

In the same manner as described in Example 1, 75 g of chitosan powder having a molecular weight of 145,000 and a deacetylation degree of 89.4%, which was obtained from a prawn shell, was added to 425 g of a 1N aqueous solution of acetic acid to obtain a chitosan solution having a concentration 15% by weight. Formation of a chitosan membrane was tried by using the obtained chitosan solution under the same conditions as described in Example 1. However, since the viscosity of this chitosan solution was too high, formation of a membrane using an applicator was impossible.

We claim:

1. A membrane for the separation of a water-alcohol mixed liquid by the pervaporation method, which is composed of a chitosan having a molecular weight of 80,000 to 150,000 and a deacetylation degree adjusted to 80 to 95%.

2. A separating membrane as set forth in claim 1, wherein the chitosan is crosslinked.

3. A separating membrane as set forth in claim 1, which is in the form of a flat membrane.

4. A separating membrane as set forth in claim 1, which is in the form of a hollow tube or fiber membrane.

5. A process for the preparation of a separating membrane as set forth in claim 1, which comprises dissolving a chitosan having a molecular weight of 80,000 to 150,000 and a deacetylation degree adjusted to 80 to 95% in an acidic aqueous solution to form a dope having a chitosan concentration of 9 to 12% by weight, shaping the dope into a membrane and immersing the membrane in an alkaline solution.

6. A process for the separation of a water-alcohol mixed liquid, wherein the separation is carried out by using a separating membrane as set forth in claim 1 by the pervaporation method.

7. The process of claim 6 wherein the alcohol in the water-alcohol mixed liquid is methanol.

8. The process of claim 6 wherein the alcohol in the water-alcohol mixed liquid is ethanol.

9. The process of claim 6 wherein the alcohol in the water-alcohol mixed liquid is isopropanol.

10. The process of claim 6 wherein the separating membrane is in the form of a flat membrane.

11. The process of claim 6 wherein the separating membrane is in the form of a hollow tube or fiber membrane.

12. A separating membrane as set forth in claim 1 wherein the chitosan has a molecular weight of from about 90,000 to 120,000 and a deacetylation degree of about 95%.

13. A separating membrane as set forth in claim 1 wherein the chitosan has a molecular weight of from about 105,000 to 145,000 and a deacetylation degree of about 89 to 90%.

* * * * *